United States Patent [19]

Artiss et al.

[11] Patent Number: 4,626,511
[45] Date of Patent: Dec. 2, 1986

[54] COMPOSITION FOR REDUCING TURBIDITY IN SAMPLES OF BIOLOGICAL FLUIDS

[75] Inventors: Joseph D. Artiss, Windsor, Canada; Bennie Zak, Southfield, Mich.

[73] Assignee: Wayne State University, Detroit, Mich.

[21] Appl. No.: 733,267

[22] Filed: May 13, 1985

[51] Int. Cl.⁴ .......................................... G01N 31/00
[52] U.S. Cl. ........................................ 436/8; 436/18; 436/13; 436/15
[58] Field of Search ............... 435/4, 11, 17, 19, 18, 435/25, 28, 188; 436/8-19; 252/408.1; 424/3, 11, 7.1

[56] References Cited

U.S. PATENT DOCUMENTS

| | | | |
|---|---|---|---|
| 3,168,448 | 2/1965 | Melcer et al. | 195/66 |
| 3,260,648 | 7/1966 | Fox | 167/84 |
| 3,703,591 | 11/1972 | Bucolo et al. | 195/103 R |
| 3,759,793 | 9/1973 | Stork et al. | 195/103 R |
| 3,853,465 | 12/1974 | Rush et al. | 23/230 B |
| 4,011,045 | 3/1977 | Bonderman | 23/230 B |
| 4,012,287 | 3/1977 | Carl et al. | 195/103 R |
| 4,066,508 | 1/1978 | Rauscher et al. | 195/99 |
| 4,216,117 | 8/1980 | Proksch et al. | 436/13 |
| 4,245,041 | 1/1981 | Denney | 435/15 |
| 4,309,502 | 1/1982 | Lauderdale | 435/15 |
| 4,338,395 | 7/1982 | Leon et al. | 435/17 |
| 4,370,311 | 1/1983 | Ilekis | 436/13 |
| 4,465,774 | 8/1984 | Huang et al. | 436/13 |
| 4,486,531 | 12/1984 | Ziegenhorn et al. | 436/13 |
| 4,489,162 | 12/1984 | Hawkins et al. | 436/15 |
| 4,503,146 | 3/1985 | Yun et al. | 436/13 |

FOREIGN PATENT DOCUMENTS 8303680 10/1983 World Int. Prop. O. ........... 436/13

Primary Examiner—John F. Terapane
Assistant Examiner—T. J. Wallen
Attorney, Agent, or Firm—Basile, Weintraub & Hanlon

[57] ABSTRACT

A composition which reduces the turbidity of samples of artificial or naturally occurring biological fluids comprising:
 a buffering agent;
 a nonionic surfactant;
 alpha-cyclodextrin;
 a lipase; and
 water.

The composition provides a catalyst for and agents which hydrolyze triglycerides present in the sample to glycerol and free fatty acids. Also present in the composition is a complexing agent or agents to render the catalyzed fatty acids water-soluble.

21 Claims, 3 Drawing Figures

COMPOSITION FOR REDUCING TURBIDITY IN SAMPLES OF BIOLOGICAL FLUIDS

BACKGROUND OF THE INVENTION

1. Field of the Invention

The present invention relates to a means and method of analyzing naturally occurring and artificially produced biological fluids. More particularly, the present invention concerns a means and method of reducing turbidity in various biological samples for other biological assays, for example hemoglobin determination.

2. Prior Art

Many assays of biological fluids such as glucose, albumin, etc., in whole blood or plasma, require colorimetric methods of analysis. In such samples, elevated triglyceride levels interfere with accurate determinations by causing sample turbidity which poses problems during analysis. One such example of this is during hemoglobin determination.

Blood assays to determine total blood hemoglobin are a necessary element of medical blood work-ups. To ascertain the hemoglobin content of blood, hemoglobin is conventionally converted to cyanomethemoglobin using Drabkin's reagent. However, the presence of elevated levels of triglycerides in both whole blood and plasma samples causes turbidity during conventional analysis. The turbidity created by the triglycerides in the samples creates difficulties in determining the hemoglobin content of the sample. Turbidity also has deleterious effects on samples requiring optical analysis and in radioimmuno assays.

To overcome problems of turbidity many means and methods have been developed. Presently, the predominant approaches are ultra-centrifugation, organic solvent extraction or chemical precipitation of the lipoproteins. These are time-consuming, arduous and cumbersome techniques.

Exemplifying the prior art is, for example, U.S. Pat. No. 4,309,502. This patent teaches a reagent kit for the hydrolysis of triglycerides to glycerol and free fatty acids using lipase, and at least one reagent capable of assaying glycerol. The invention disclosed in this reference is predicated on the use of a microbial source of lipase such as *Chromobacterium viscosum*, which, in turn, requires activation by the presence of a surfactant.

Other relevant art is found in U.S. Pat. Nos. 4,338,395; 3,168,448; 3,759,793; 4,245,041; 3,703,591; 4,012,287 and 3,853,465.

In McGowan, et al., *Clinical Chemistry*, Volume 29, No. 3, 1983, there is described a totally enzymatic technique for measuring triglycerides involving the complexation of generated fatty acids thus eliminating the production of turbidity.

None of the prior art is directed to the elimination of triglycerides to reduce the turbidity generated thereby. It is to be appreciated that the prior art fails to provide a simple, one-step reagent which overcomes the turbidity in samples of biological fluids to permit sample assaying. It is to this purpose that the present invention is directed.

SUMMARY OF THE INVENTION

In accordance with the present invention there is provided a reagent composition for reducing turbidity in samples of artificial or naturally occurring biological fluids comprising:

(a) a buffering agent;
(b) a nonionic surfactant;
(c) cyclodextrin;
(d) lipase; and
(e) water.

The reagent of the present invention, when added to whole blood, serum or plasma, reduces turbidity and permits accurate measurement of hemoglobin, albumin, glucose and total protein in lipemic whole blood, serum and plasma samples. Likewise, the present composition can be used to reduce turbidity caused by triglycerides in other naturally occurring or artificial biological fluids.

In use, the reagent composition can be added directly to the sample to be analyzed to clarify the sample. The reagent composition can be admixed with conventional colorimetric indicators such as Drabkin's reagent and the modified reagent added to the sample to be analyzed. The reagent composition hereof can be applied to automated instrumentation without deleterious affects.

For a more complete understanding of the present invention, reference is made to the following detailed description and accompanying examples.

DESCRIPTION OF THE PREFERRED EMBODIMENTS

Figure 2:
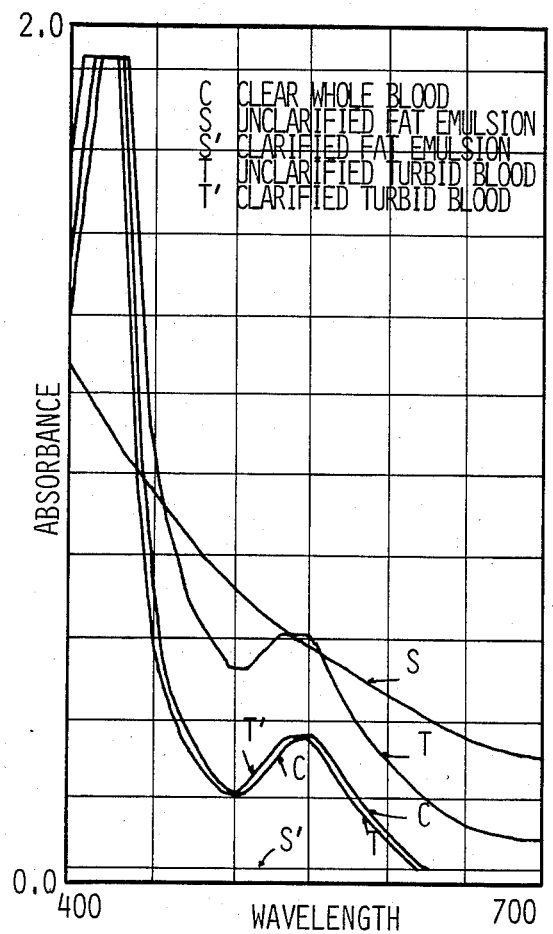

In accordance with the present invention there is provided a reagent for reducing turbidity in biological fluids and, in particular, in lipemic whole blood, serum or plasma or other biological fluids, to permit hemoglobin, albumin, glucose and total protein analysis. The reagent of the present invention comprises:

(a) a buffering agent;
(b) a nonionic surfactant;
(c) cyclodextrin;
(d) lipase; and
(e) water.

It is to be appreciated by those skilled in the art to which the present invention pertains that the reagent of the present invention can be admixed with various conventional analytical reagents such as Drabkin's reagent and the like. Drabkin's reagent is a well-known reagent for assaying hemoglobin which is an admixture of potassium ferricyanide and an alkali metal cyanide, preferably, either potassium or sodium cyanide.

The buffering agent employed in the present invention can be any well-known buffering agent which renders the total solution slightly alkaline, i.e., having a pH greater than about 7. Representative of the buffering agents which can be used herein include sodium carbonate, sodium bicarbonate, calcium carbonate, sodium hydroxide, potassium phosphate, sodium phosphate and the like, as well as mixtures thereof. The buffering agent selected will vary depending upon the analyte and type of biological fluid solution to be analyzed.

As is reported in U.S. Pat. No. 4,011,045, the addition of a nonionic surfactant aids in the dissolution of triglycerides. Nonionic surfactants serve to activate or catalyze the lipase which promotes the decomposition of triglycerides to glycerol and free fatty acids. Preferably, a nonionic surfactant, such as an ethylene oxide adduct of an alkyl phenol is employed. These surfactants are well known and commercially available, such as the ethylene oxide adduct of a nonylphenol sold by Rohm & Hoss under the name Triton X-100. Likewise, ethylene oxide adducts of an octyl phenol can be employed herein.

Cyclodextrin is employed as a fatty acid scavenger or complexing agent to render the lipase-generated fatty acids water-soluble. This enables the clarification of the sample directly without the need for separation of the lipids from the sample. Cyclodextrin is a commercially available product and is well known. Either alpha-, beta- or gamma-cyclodextrin or mixtures thereof can be employed in the present invention.

Finally, in practicing the present invention, a lipase is used in admixture with the other components of the reagent hereof. The lipase, is, of course, an enzyme of microbial origin which hydrolyzes the triglycerides. Preferably, the lipase employed herein is of *Chromobacterium viscosum*.

The utilization of the lipase involves the efficient and rapid catalysis of the hydrolysis of the triglycerides to glycerol and free fatty acids. The advantage of lipase is that this enzyme provides for clarification of the serum over a broad pH range from about 3 to about 10 in a period less than or equal to five minutes; the time required for most colorimetric reactions.

In preparing the reagent composition of the present invention, generally, from about 3,000 to 4,000 KU of the lipase per liter of the buffered aqueous solution is employed. Preferably, from about 3,300 to about 3,700 KU of lipase is employed.

Cyclodextrin is employed in an amount ranging from about 1.0 grams to about 10.0 grams per liter of buffered aqueous solution and is preferably present in an amount ranging from about 3.0 grams to about 8.0 grams thereof per liter of reagent.

The surfactant is employed in an amount ranging from about 0.1 to about 1.0 grams thereof per liter of buffered aqueous solution and is, preferably, present in an amount ranging from about 0.25 to about 0.75 grams thereof per liter of the buffered aqueous solution.

The buffering agent is employed in an amount just sufficient to yield a solution pH optimal for the analysis to be performed.

In preparing the reagent composition hereof the components are admixed together under ambient conditions.

In practice, the addition of the composition of the present invention to samples, plasma, serum or other biological fluids, directly results in the reduction of turbidity of the sample by the direct hydrolysis of the triglycerides to glycerol and free fatty acids and the subsequent complexation of the fatty acids by the cyclodextrin.

When analyzing whole blood hemoglobin, the composition of the present invention is admixed with conventional Drabkin's reagent. When a blood sample is added, the clearing of the triglycerides occurs within the known period for the reaction of hemoglobin with potassium ferricyanide and potassium cyanide to yield cyanmethemoglobin and the admixture does not interfere with that reaction.

For a more complete understanding of the present invention reference is made to the following examples. The examples are intended to be illustrative and not limitative of the present invention.

ANALYTICAL PROCEDURE

In the following examples of the present invention, the reagent hereof is employed in an additive to a conventional colorimetric reagent, i.e., Drabkin's reagent. In carrying out the examples, a stock solution based upon one liter of Drabkin's reagent was employed. To one liter of Drabkin's reagent was added the reagent hereof which has the following composition:

3,400 KU of lipase;
4.0 grams of alpha-cyclodextrin;
0.5 grams Triton X-100;
1.0 gram of sodium bicarbonate.

This mixture is stable for at least six weeks when stored refrigerated in a dark bottle.

In practicing the present invention, the blood and serum samples used were freshly discarded samples obtained from a hemotology laboratory.

Grossly lipemic whole blood was prepared by resuspending saline-washed red cells in either an intravenous fat emulsion or a triglyceride-rich serum having triglyceride concentrations of about 70 grams per liter. Chylomicrons were harvested by separating them from severely lipemic serums in which the refrigeration test showed marked elevations.

The determination of hemoglobin in the lipemic blood was carried out by adding five microliters (5 $\mu$l) of a blood sample to one and a half milliliters (1.5 ml.) of the modified Drabkin's reagent. The solution was then thoroughly mixed and incubated at 37° C. for a minimum of five minutes.

The absorbance of the sample was measured at 540 nanometers (nm) using a Model 25 Beckman spectrophotometer equipped with a flow-through, thermostated microcuvet. The absorbances of the samples and standard at 540 nm was measured versus a reagent blank in which deionized water was substituted for the sample.

EXAMPLE I

Figure 1:
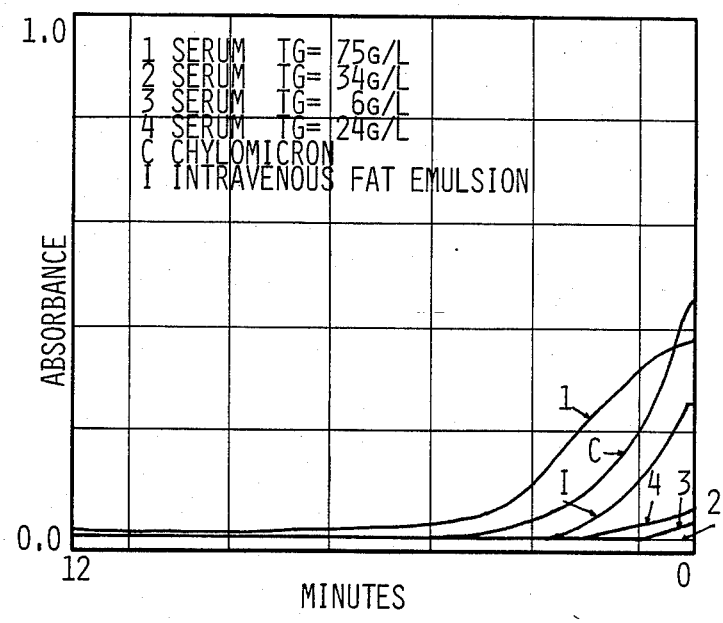

In order to study the clarification potential of the Drabkin's reagent modified by the present invention, the catalytic activity of the formulation of Example I on different turbid substrates was determined by measuring the decrease in absorbance at the hemoglobin peak of 540 nm. The results are graphed in FIG. 1. The substrates of clinical interest were chylomicrons (C), intravenous fat emulsion (i) and several serums containing triglycerides at concentrations of 6 g/L, 24 g/L, 34 g/L and 75 g/L respectively. The samples having low level triglyceride contents were clarified very quickly. All assays showed transparent characteristics on spectral inspection after five minutes. Clarification of all lipemic serum samples occurred within five minutes of treatment. Thus, under these conditions, clarification of the sample specimens occurs within the time limit required for the conversion of hemoglobin to cyanmethemoglobin, which also takes approximately five minutes for completion.

EXAMPLE II

To demonstrate that the components of the modified Drabkin's reagent of the present invention do not interfere in the formation of cyanmethemoglobin, the modified Drabkin's reagent was applied to two clear, whole blood samples. In the samples, the plasma was totally replaced with either a solution of total parenteral nutrition or a severely lipemic serum. The typical spectra obtained are shown in FIG. 2. The post clarification spectrum (T') is that of the original clear sample (C) indicating the absence of any interference with cyanmethemoglobin formation.

EXAMPLE III

Figure 3:
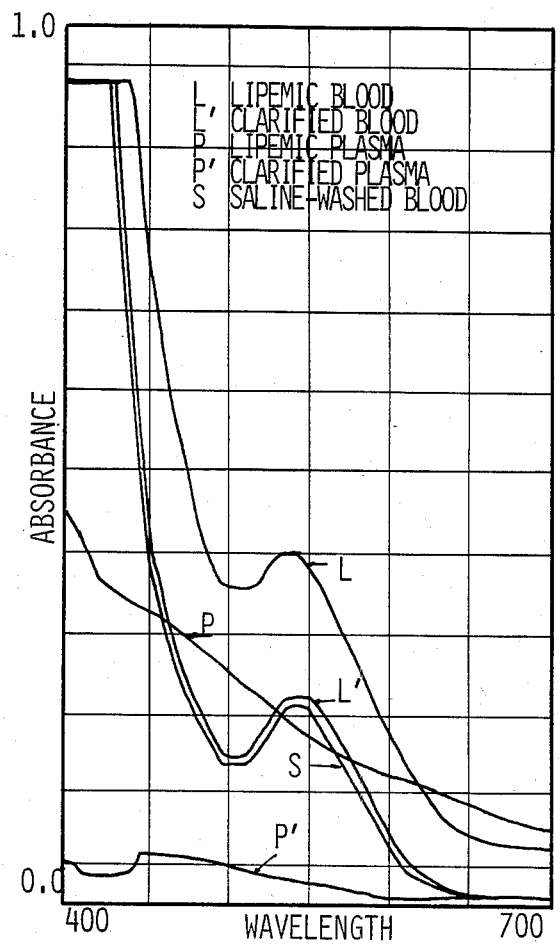

A severely lipemic whole blood specimen was treated with the modified Drabkin's reagent of the present invention. The results are set forth in FIG. 3. The lines designated P and P' are the spectra of the plasma before and after enzymic clarification and alphacyclodextrin fatty acid scavenging. In like manner, spectrum L is the original specimen treated with un-modified Drabkin's reagent where L' is the clarified specimen and S is saline-washed whole blood.

EXAMPLE IV

The applicability of the present invention to determine hemoglobin was next studied using:

(i) a hemoglobin solution having a hemoglobin concentration of 140 grams per liter prepared from washed erythrocytes and diluted with sera of different turbidities thus simulating lipemic whole blood; and (ii) whole blood from hyperlipidemic patients.

The results are shown in Table I.

As set forth in Table I, the turbidity resulting from elevated triglyceride concentrations can cause significant increase in the hemoglobin values. The sample diluted with chylomicrons showed the largest increase in absorbance, suggesting that hemoglobin values are significantly elevated in hyperlipidemic specimens.

The results of hemoglobins assays in lipemic patient specimens is shown in Table II. The post-clarification hemoglobin value corresponds closely to the recommended procedure of re-suspending the red cells in clear serum or physiological saline; methods previously described and recommended in the literature.

Thus, it can be seen from the five examples that the modified Drabkin's reagent and method of employing it reduce sample turbidity and determine hemoglobin content of blood samples provides an accurate and efficient method of blood analysis.

TABLE I

Cleared and uncleared hemoglobin values for samples prepared by diluting a hemoglobin solution (140 g/L) 1:1 with various sera.

| Media | Absorbance* | | Hemoglobin (g/L)* | |
|---|---|---|---|---|
| | Uncleared | Cleared | Uncleared | Cleared |
| Chylomicrons | 0.634 | 0.156 | 280 | 69 |
| Turbid serum (triglyceride = 33.6 g/L) | 0.202 | 0.161 | 89 | 71 |
| Turbid serum (triglyceride = 12.5 g/L) | 0.239 | 0.162 | 105 | 71 |
| Turbid serum (triglyceride = 5.74 g/L) | 0.170 | 0.160 | 75 | 71 |
| Clear serum | 0.162 | 0.162 | 71 | 71 |
| Clear serum | 0.162 | 0.159 | 71 | 70 |
| Clear serum | 0.161 | 0.161 | 71 | 71 |

*Average of duplicate values

TABLE II

Hemoglobin values for patient specimens (lipemic whole blood) before and after clarification and compared to the recommended procedure of plasma replacement with saline.

| | Hemoglobin Concentration (g/L)* | | |
|---|---|---|---|
| | Patient Whole Blood | | |
| No. | Uncleared | Cleared | RBC in Saline |
| 1 | 157 | 145 | 144 |
| 2 | 125 | 107 | 108 |
| 3 | 111 | 104 | 102 |
| 4 | 202 | 122 | 112 |

*Average of triplicates.

We claim:

1. A composition for reducing turbidity in biological fluid samples consisting essentially of:
   a buffering agent;
   a lipase-activating nonionic surfactant;
   cyclodextrin;
   a lipase; and
   water.

2. The composition of claim 1 wherein the buffering agent is selected from the group consisting essentially of sodium carbonate, sodium bicarbonate, calcium carbonate, sodium hydroxide, potassium phosphate, sodium phosphate or mixtures thereof.

3. The composition of claim 1 wherein the buffering agent is sodium bicarbonate.

4. The composition of claim 1 wherein the nonionic surfactant is an ethylene oxide adduct of an alkyl phenol.

5. The composition of claim 1 wherein the nonionic surfactant is an ethylene oxide adduct of a nonyl phenol.

6. The composition of claim 1 wherein the nonionic surfactant is an ethylene oxide adduct of an octyl phenol.

7. The composition of claim 1 wherein the lipase is derived from *Chromobacterium viscosum*.

8. The composition of claim 1 wherein the lipase is present at a concentration in the range of about 3000 to about 4000 KU of lipase per liter of water.

9. The composition of claim 8 where the lipase is present in the range of about 3,300 to about 3,700 KU.

10. The composition of claim 1 wherein the cyclodextrin is selected from the group consisting of alpha-cyclodextrin, beta-cyclodextrin, gamma-cyclodextrin or mixtures thereof.

11. The composition of claim 10 wherein the cyclodextrin is employed in an amount ranging from about 1.0 grams to about 10.0 grams per liter of water.

12. The composition of claim 10 wherein the cyclodextrin is employed in an amount ranging from about 3.0 to about 8.0 grams per liter of water.

13. The composition of claim 1 wherein the cyclodextrin is alpha-cyclodextrin.

14. The composition of claim 1 wherein the cyclodextrin is beta-cyclodextrin.

15. The composition of claim 1 wherein the cyclodextrin is gamma-cyclodextrin.

16. The composition of claim 1 wherein the surfactant is employed in an amount ranging from about 0.1 to about 10 grams per liter of water.

17. The composition of claim 16 wherein the surfactant is present in an amount ranging from about 0.25 to about 0.75 grams per liter of water.

18. The composition of claim 1 wherein the buffering agent is employed in an amount sufficient to yield a solution pH at or above 7.

19. The composition of claim 1 wherein the solution has a pH in the range between about 8 and about 9.

20. A composition for reducing turbidity in samples of biological fluids consisting essentially of:
- a buffering agent selected from the group consisting essentially of sodium carbonate, sodium bicarbonate, calcium carbonate, sodium hydroxide, potassium phosphate, sodium phosphate or mixtures thereof;
- an ethylene oxide adduct of nonylphenol;
- cyclodextrin selected from the group consisting essentially of alpha-cyclodextrin, beta-cyclodextrin, gamma-cyclodextrin, or mixtures thereof;
- a lipase derived from *Chromobacterium viscosum;* and water.

21. A composition for reducing the turbidity of hemoglobin containing samples consisting essentially of:
- potassium ferricyanide;
- an alkali metal cyanide, selected from the group consisting essentially of potassium cyanide and sodium cyanide;
- sodium bicarbonate;
- an ethylene oxide adduct of a nonylphenol;
- alpha-cyclodextrin;
- a lipase derived from *Chromobacterium viscosum;* and water.

* * * * *